United States Patent [19]
Wambebe et al.

[11] Patent Number: 5,840,310
[45] Date of Patent: Nov. 24, 1998

[54] PHYTODRUG FOR TREATING SKIN FUNGAL INFECTIONS AND METHODS OF PREPARING AND USING SAME

[75] Inventors: Charles O. N. Wambebe; Nkechi M. Enwerem, both of Abuja; Ibrahim Kolo, Suleja; Shingu K. Gamaniel, Abuja, all of Nigeria

[73] Assignee: National Institute For Pharmaceutical Research and Development, Abuja, Nigeria

[21] Appl. No.: 906,832

[22] Filed: Aug. 6, 1997

[51] Int. Cl.⁶ ..................................................... A01N 65/00
[52] U.S. Cl. ............................................................ 424/195.1
[58] Field of Search ........................................... 424/195.1

[56] References Cited

U.S. PATENT DOCUMENTS 4,309,207  1/1982  Devlin .................................. 424/195.1

OTHER PUBLICATIONS

Derwent Abstract –86–270030/41 Buzogany et al RO—89061 Apr. 30, 1986.

Derwent Abstract –93–278182/35 Pola Chem IND Inc JP05194177 Aug. 03, 1993.

*Primary Examiner*—Herbert J. Lilling
*Attorney, Agent, or Firm*—Shook, Hardy & Bacon, L.L.P.

[57] ABSTRACT

A phytochemical composition for treating skin fungal infections is provided. The composition is an organic solvent extract of dried, coarsely ground *Mitra villosus* plant leaves. The extract may be prepared using a hot soxhlet extraction process using hexane as the extraction solvent. The extract is admixed with an excipient base to form an ointment and the ointment is applied topically to areas of skin which are infected with fungal infection. Also described are methods for making the extract and methods for using the extract.

29 Claims, No Drawings

5,840,310

PHYTODRUG FOR TREATING SKIN FUNGAL INFECTIONS AND METHODS OF PREPARING AND USING SAME

BACKGROUND OF THE INVENTION

1. Field of the Invention

The present invention relates to the field of phytodrugs, and in particular the invention relates to phytodrugs for treating skin fungal infections and methods of preparing and using same.

2. Prior Activities and Problems in the Field

The need to develop new antifungal agents has become relevant in the light of significant toxicity, high cost and non-availability of existing antifungal drugs. In particular, there is a desire on the part of some to develop and commercialize new herbal remedies for dermatomycoses utilizing a blend of existing and new knowledge derived from collaborations between modern scientists and traditional African healers.

Nigeria has a very strong traditional medical practice where the traditional healers play a major role as health care providers in both urban and rural settings. These traditional practitioners are knowledgeable regarding the use of plants and plant extracts for healing purposes. Moreover, there is a large reservoir of medicinal plants with potential chemotherapeutic constituents. This combination is valuable in the search for new drug remedies based on ethnomedical information.

SUMMARY OF THE INVENTION

In accordance with the present invention, a new drug material extracted from *Mitra villosus* (family: Rubiaceae) plant leaves has been found to be effective in treating fungal infections. In particular the invention provides a new composition for treating skin fungal infections comprising an organic solvent extract of *Mitra villosus* plant leaves. In one preferred embodiment of the invention, the extract may comprise a hexane extract of *Mitra villosus* plant leaves. Preferably, the extract may comprise a hot hexane soxhlet extraction procedure extract of *Mitra villosus*. The extract may also comprise a methanol extract of *Mitra villosus*.

The invention also provides a method for preparing a composition for treating skin fungal infections which comprises drying *Mitra villosus* plant leaves, reducing the dried leaves to a coarse powder, and subjecting the coarse powder to an extraction process to thereby form an extract containing a drug material effective for treating said skin fungal infections. The drying step may consist of air drying the *Mitra villosus* plant leaves using a fan to circulate air over the leaves. Preferably, the drying step comprises drying the *Mitra villosus* plant leaves in an open environment using atmospheric air.

In accordance with the invention the dried leaves may be ground using a wooden mortar and pestle to produce a coarse powder. Alternatively, the dried leaves may be ground into a coarse powder using a hammer mill. Preferably, hexane may be used as an extraction solvent in said extraction process. In particular the extraction process may be a hot hexane soxhlet extraction process. The extraction may also be conducted using methanol.

Also provided by the invention is an ointment which may be used for treating skin fungal infections. The ointment may be made up of a powdered organic solvent extract of *Mitra villosus* plant leaves and an excipient carrier for said extract. Preferably the extract is a hot hexane soxhlet procedure extract of *Mitra villosus* plant leaves. The excipient carrier may comprise an emulsifying ointment base made up of a mixture of an emulsifying wax, white soft paraffin and liquid paraffin. In preferred forms of the invention the emulsifying ointment base may comprise about 30% by weight of said emulsifying wax, about 50% by weight of said white soft paraffin and about 20% by weight of said liquid paraffin, and the ointment itself may contain about 1 to 5% by weight of said extract.

For its major objective, the invention provides a method for treating humans afflicted with skin fungal infections. Such treatment methodology may comprise providing a batch of dried, coarsely powdered *Mitra villosus* plant leaves, subjecting said batch of leaves to an extraction process using an organic extraction solvent to thereby form an extract of said *Mitra villosus* plant leaves effective for treating said skin fungal infection, and treating a human afflicted with a skin fungal infection by applying an effective amount of said drug material topically to an infected skin area of said human.

Finally the invention provides a method for treating skin fungal infections wherein an organic extract of dried and coarsely ground *Mitra villosus* plant leaves is mixed with an emulsifying ointment base to form an ointment and such ointment is spread topically on an infected area of the skin. Preferably, the ointment may comprise about 1 to 5% by weight of said extract.

DETAILED DESCRIPTION OF PREFERRED EMBODIMENTS OF THE INVENTION

In accordance with the invention, a composition for treating and managing skin fungal infections is provided. The composition is prepared by extracting effective antifungal phytochemicals from the dried and ground leaves of *Mitra villosus* plant. In a preferred form of the invention, the dried, ground leaves are subjected to a hot soxhlet extraction process using n-hexane as an extraction solvent. The extract may be combined with an excipient oil base carrier material to prepare an ointment. The ointment, which may preferably contain from about 1 to about 5% of the extract by weight, is preferably applied topically and directly to areas of the skin which are infected by fungus.

*Mitracarpus villosus* was selected as a possible candidate for scientific investigation and its effectiveness against fungi was determined. Antifungal activity was assessed against *Candida albicans, Tricophyton mentagrophytes, Microsporum canis, Epidermophyton flocossum,* and *Tricophyton rubrum,* using the Agar dilution method. These organisms were chosen because they are usually responsible for superficial mycoses in man. The results indicate that *Mitra villosus* plant leave extract has potential to be very useful in treating and managing fungal infections of the skin. For example, the product inhibited growth of all the organisms tested in vitro.

Anti-inflammatory and antimicrobial activities of the extract were also studied. From the results, the product may have anti-inflammatory properties but no antibacterial effects were observed. Acute toxicity studies in laboratory animals showed an $LD_{50}$ of 980 mg/kg intraperitoneally in mice suggesting that it may be safe even when taken orally by accident.

The *Mitra villosus* plant leave extract may be prepared using an extraction process as described hereinafter. The plant leave material is first dried in an open atmosphere using a fan to circulate atmospheric air. The dried plant leave material is then reduced to a coarse powder using a hammer mill (1 kg) or a wooden mortar and pestle (700 g). The powdered material is loaded into a 2 L soxhlet extractor mounted on a 2 L quick fit distillation flask containing the desired solvent. At the top of the extractor is fixed a double surface condenser through which tap water (22°±3° C.) is circulated. The solvent in the flask is heated on a steam bath (or a carefully regulated heating mantle). The solvent vaporizes and rises up the arm of the extractor into the cold condenser and drops as a liquid onto the packed plant material.

The solvent then percolates through the plant material, it extracts soluble components and rises up in the extractor until the last air bubble is pushed out of the inner siphon tube. The solution of extract now siphons into and collects in the distillation flask with continued heating. The process is repeated as the extract leaves the plant material and is concentrated in the flask. After extraction is completed (16–24 hours with hexane; 10–14 hours with methanol), the solvent is distilled off and the crude extract concentrate is decanted into a weighed, labelled beaker (100 ml, 250 ml or 400 ml, as desired) and allowed to dry completely in air or dessicator. The solvent may be effectively removed using a rotary evaporator.

The plant material meanwhile is removed from the extractor and placed on a polyethylene sheet on top of the lab bench to dry completely. It is then loaded again and extracted with the next solvent of choice (of higher polarity). Extraction is usually first done with hexane (or petroleum spirit, 60°–80° C.) followed by ethylacetate or dichloromethane. Hexane/Petroleum ether extracts metabolites that are non-polar (defatting). Dichloromethane/Ethyl acetate removes slightly polar components.

With a 1 L or 250 ml soxhlet extractor, siphoning is more frequent and less extraction time is required. With a 250 ml extractor, for example, extraction with hexane may be complete in 10–12 hours while extraction with methanol may last for 6–8 hours.

The approximate ranges of yield percentages are as follows:

Hexane extraction solvent=0.05–0.1%

Methanol extraction solvent=0.07–0.13%

The phytochemical analysis of the plant extract revealed the presence of alkaloids, saponins, flavonoids, glycosides, tannins, volatile oil and general anthraquinones. The extract contains approximately 0.03 to 0.05% by weight of volatile oils, about 0.00014 to 0.00018% by weight of steroids and about 0.0022 to 0.0024% by weight of triterpenoids. However, the specific concentrations of alkaloids, saponins, flavanoids, glycosides, tannin, and general anthraquinone have not yet been determined.

The dried extract may be formulated into an ointment. The preferred excipient base is an emulsifying ointment base. The composition of the excipient may preferably be as follows:

Emulsifying wax—about 30% by weight

White soft paraffin—about 50% by weight

Liquid paraffin—about 20% by weight

The concentration of the dried leaf extract of *M. villosus* in the antifungal cream may preferably range from about 1% by weight to about 5% by weight.

The ointment is applied to the clean surface of skin in two divided doses, i.e. morning and evening.

The effectiveness of the extract against organisms which are known to be responsible for superficial mycoses, such as *Epidermophyton flocossum* ATCC 10227, (EF); *Microsporum canis* ATCC 11622, (MC); *Tricophyton rubrum* ATCC 28941, (TR); *Tricophyton mentagrophytes* ATCC 4808 (TM), was tested as follows. The dried and ground *M. villosus* plant leave material was subjected to extraction using four different extraction solvents, namely n-hexane, methanol, cold water and hot water.

The percent yields of the different extracts of the fresh leaves of *M. villosus* are indicated below:

| SOLVENT | % YIELD |
| --- | --- |
| n-Hexane | 1.56 |
| Methanol | 2.3 |
| Hot water | 1.69 |
| Cold water | 0.55 |

Agar dilution method was employed for the plant extracts. Double dilutions of the extracts were used in all cases starting with 1000 µg per milliliter of Sabouraud Dextrose Agar. The following tables illustrate the effectiveness of the extract against the organisms and compares the efficiency of the different extraction solvents.

| | Organisms | | | |
| --- | --- | --- | --- | --- |
| Concentrations (Ug/ml) | TM | MC | EF | TR |
| I. HEXANE EXTRACTION | | | | |
| 1000 | − | − | − | − |
| 500 | − | − | − | − |
| 250 | − | + | − | + |
| 125 | + | + | + | + |
| II. METHANOL EXTRACTION | | | | |
| 1000 | − | − | − | − |
| 500 | + | + | + | + |
| 250 | + | + | + | + |
| 125 | + | + | + | + |
| III. COLD WATER EXTRACTION | | | | |
| 1000 | + | + | + | + |
| 500 | + | + | + | + |
| 250 | + | + | + | + |
| 125 | + | + | + | + |

Similar result of no activity was also recorded for the hot water extraction.
KEY:
− = No growth, i.e. growth of organism was inhibited.
+ = Growth of organism.

Two separate formulations of ointment based on *M. villosus* plant leave extract were developed at laboratory scale and these were tested on patient volunteers. Twelve patients participated in the limited clinical trials to assess the efficacy and safety of *M. villosus* extract against fungal skin infections. The ointment was applied topically to the infected skin area twice daily. Ten of the patients recovered fully. In those that recovered, itching stopped and pain disappeared. Some of the patients were able to wear shoes comfortably. No adverse side effects have been observed thus far.

We claim:

1. A composition for treating skin fungal infections comprising an organic solvent extract of *Mitra villosus* plant leaves.

2. A composition as set forth in claim 1 comprising a hexane extract of *Mitra villosus* plant leaves.

3. A composition as set forth in claim 1 comprising a methanol extract of *Mitra villosus* plant leaves.

4. A composition as set forth in claim 2 comprising a hot hexane soxhlet procedure extract of *Mitra villosus* plant leaves.

5. A method for preparing a composition for treating skin fungal infections comprising:

drying *Mitra villosus* plant leaves;

reducing the dried leaves to a coarse powder; and subjecting the coarse powder to an extraction process to thereby form an extract containing a drug material effective for treating said skin fungal infections.

6. A method as set forth in claim 5, wherein said drying step comprises air drying the *Mitra villosus* plant leaves using a fan to circulate air over the leaves.

7. A method as set forth in claim 6, wherein said drying step comprises drying said *Mitra villosus* plant leaves in an open environment using atmospheric air.

8. A method as set forth in claim 5, wherein said reducing step comprises grinding the dried leaves with a wooden mortar and pestle.

9. A method as set forth in claim 5, wherein said reducing step comprises grinding the dried leaves with a wooden mortar and pestle.

10. A method as set forth in claim 5, wherein said reducing step comprises grinding the dried leaves using a hammer mill.

11. A method as set forth in claim 5, wherein hexane is used as an extraction solvent in said extraction process.

12. A method as set forth in claim 5, wherein methanol is used as an extraction solvent in said extraction process.

13. A method as set forth in claim 5, wherein said extraction process comprises a hot soxhlet extraction process.

14. A method as set forth in claim 13, wherein hexane is used as an extraction solvent in said extraction process.

15. An ointment for treating skin fungal infections comprising a powdered organic solvent extract of *Mitra villosus* plant leaves and an excipient carrier for said extract.

16. An ointment as set forth in claim 15, wherein said extract comprises a hexane extract of *Mitra villosus* plant leaves.

17. An ointment as set forth in claim 15, wherein said extract comprises a methanol extract of *Mitra villosus* plant leaves.

18. An ointment as set forth in claim 16, wherein said extract comprises a hot hexane soxhlet procedure extract of *Mitra villosus* plant leaves.

19. An ointment as set forth in claim 15, wherein said excipient carrier comprises an emulsifying ointment base.

20. An ointment as set forth in claim 19, wherein said emulsifying ointment base comprises a mixture of an emulsifying wax, white soft paraffin and liquid paraffin.

21. An ointment as set forth in claim 20, wherein said emulsifying ointment base comprises about 30% by weight of said emulsifying wax, about 50% by weight of said white soft paraffin and about 20% by weight of said liquid paraffin.

22. An ointment as set forth in claim 15, which comprises about 1 to 3% by weight of said extract.

23. An ointment as set forth in claim 21, which comprises about 1 to 3% by weight of said extract.

24. A method for treating a human afflicted with skin fungal infection comprising:

providing a batch of dried, coarsely powdered *Mitra villosus* plant leaves;

subjecting said batch to an extraction process using an organic extraction solvent to thereby form an extract of said *Mitra villosus* plant leaves effective for treating said skin fungal infection; and treating a human afflicted with a skin fungal infection by applying said drug material topically to an infected skin area of said human.

25. A method as set forth in claim 24, wherein said extraction process comprises a hot soxhlet extraction process.

26. A method as set forth in claim 25, wherein hexane is used as an extraction solvent in said extraction process.

27. A method as set forth in claim 24 wherein said extract is mixed with an emulsifying ointment base to form an ointment and said treating step comprises spreading said ointment on said infected area.

28. A method as set forth in claim 26 wherein said extract is mixed with an emulsifying ointment base to form an ointment and said treating step comprises spreading said ointment on said infected area.

29. A method as set forth in claim 28, wherein said ointment comprises about 1 to 3% by weight of said extract.

* * * * *